United States Patent [19]

Niwa et al.

[11] 4,141,790
[45] Feb. 27, 1979

[54] PROCESS FOR THE PREPARATION OF 7-AMINO-CEPHEM COMPOUNDS USING MOLD FUNGI

[75] Inventors: Tomizo Niwa; Chuhei Nojiri, both of Yokohama; Hitoshi Goi, Chiba; Shinji Miyado, Yokohama; Fumio Kai, Fujisawa; Shigeo Seki, Tokyo; Yujiro Yamada; Taro Niida, both of Yokohama, all of Japan

[73] Assignee: Meiji Seika Kaisha Ltd., Japan

[21] Appl. No.: 796,194

[22] Filed: May 12, 1977

[30] Foreign Application Priority Data

May 24, 1976 [JP] Japan ................................ 51-59198

[51] Int. Cl.² .............................................. C12D 9/04
[52] U.S. Cl. ...................................... 195/29; 195/36 C
[58] Field of Search ............................... 195/36 C, 29

[56] References Cited

U.S. PATENT DOCUMENTS

| 3,239,394 | 3/1966 | Walton | 195/36 C |
| 3,749,641 | 7/1973 | Takahashi et al. | 195/36 C |
| 3,930,949 | 1/1976 | Kutzbach et al. | 195/29 |
| 3,962,036 | 6/1976 | Liersch et al. | 195/29 |

Primary Examiner—Alvin E. Tanenholtz
Attorney, Agent, or Firm—McGlew and Tuttle

[57] ABSTRACT

Compounds are provided having the general formula I:

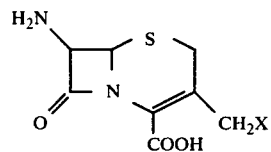

wherein X represents an hydroxyl group, an acetoxy group or a thiosulfuric acid residue. The formula I compounds are prepared from compounds of the general formula II:

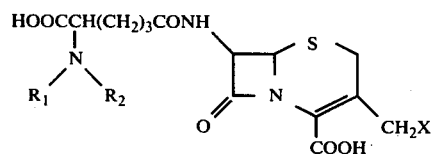

wherein $R_1$ represents hydrogen, a lower alkanoyl group, an arylalkanoyl group, an alkoxycarbonyl group, a lower haloalkoxycarbonyl group, a substituted or unsubstituted aroyl group, a N-arylcarbamoyl group of a substituted or unsubstituted aryl group; $R_2$ either represents hydrogen or, together with the

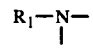

group, represents a phthalimido group; and X represents an hydroxyl group, an acetoxy group or a thiosulfuric acid residue, or their metal salts or their salts with organic bases, by causing the culture of a cephalosporin C acylase-producing strain of a microorganism, especially a mold, fungus, or the secondary preparation therefrom, to act on the latter compounds II in the presence of an aqueous medium.

8 Claims, No Drawings

PROCESS FOR THE PREPARATION OF 7-AMINO-CEPHEM COMPOUNDS USING MOLD FUNGI

BACKGROUND OF THE INVENTION

1. Field of the Invention

This invention relates to a process for the preparation of 7-amino-cephem compounds. More particularly, this invention is concerned with a process for the preparation of 7-amino-cephem compounds of the general formula I

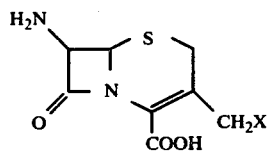

wherein X stands for a hydroxyl group, an acetoxy group or a thiosulfuric acid residue, which process is characterized by subjecting a homologue of cephalosporin C. of the general formula II:

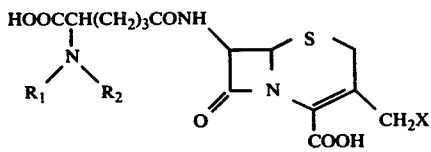

wherein $R_1$ stands for hydrogen, a lower alkanoyl group, an arylalkanoyl group, an alkoxycarbonyl group, a lower haloalkoxycarbonyl group a substituted or unsubstituted aroyl group, a N-arylcarbamoyl group or a substituted or unsubstituted aryl group, $R_2$ either means hydrogen or forms, together with the

group, a phthalimido group, and X stands for a hydroxyl group, an acetoxy group or a thiosulfuric acid residue, to an enzymatic action of the cultured mycelia of mold fungi or the secondary preparation therefrom.

For simplicity, the 7-amino-cephem compounds of the general formula I are hereinafter often referred to as "7-amino-cephem compounds I", and the homologues of cephalosporin C. of the general formula II as compounds II".

2. Prior Art

Useful antibiotics of the cephalosporin series, such as, for example, Cephalothin, Cephaloridine or Cephaloglycine, are prepared in general by converting cephalosporin C. which is obtained by the fermentation process, into 7-amino-cepharosporanic acid (hereinafter often referred to as "7-ACA") and chemically modifying the latter in an appropriate manner. Therefore, the 7-ACA compound is the most important starting material for the preparation of these cephalosporin antibiotics. Further, both Cefoxitin which is now under development as a new synthetic cephalosporin antibiotic and which is attracting public attention due to excellent effects exhibited in its evaluation testing (see Antimicrobial Agents and Chemotherapy, Vol. 5, page 25, 1974) and Cefuroxime which also is now under development and whose effects are recognized as excellent (see The Journal of Antibiotics, Vol. 29, page 29, 1976), have commonly carbamoyloxymethyl groups in the 3-positions. For the synthesis of such compounds, 3-deacetyl-7-amino-cephalosporanic acid (hereinafter often referred to as "D-7-ACA") serves as a better starting material. The D-7-ACA is also suitable as the starting material for the synthesis of 3-substituted-vinyl-cephalosporine which is attracting public attention due to their potent antibacterial effect on Gram negative bacteria (see Journal of Medical Chemistry, Vol. 18, page 986, 1975).

A number of methods for effecting in chemical manner the deacylation of cephalosporin C. at the 7-position (hereinafter often referred to, for simplicity, as "deacylation") have been hitherto proposed, and in fact the deacylation is at present carried out by chemical processes on an industrial scale. As a method for chemical deacylation of cephalosporin C. is known, for example, the iminohalide process (see Japanese Patent Publication No. Sho-41-13862). This deacylation process comprises the steps of; protection of the amino group of cephalosporin C.; protection of the carboxyl group; conversion to the iminochloride; conversion to the imino ether; deacylation; and elimination of the protective group for the carboxyl group. Since this process involves a number of reaction steps, sequential operation of the steps is very cumbersome, taking a long period of time. Further, in an attempt to improve the iminohalide process was proposed the so-called silyl chloride process (see Japanese patent Publication No. Sho-45-40899). This process is advantageous over the iminohalide process in that the process steps are fewer in number, but is accompanied by problems such as a requirement of cooling to temperatures below $-60°$ C. and high cost of the reaction apparatus and so on. In addition to these problems, the chemical deacylation processes suffer from another disadvantage that it is necessary in order to attain high yields to use high purity starting material cephalosporin C.

The theoretical possibility of the direct deacylation of cephalosporin C. by the use of microorganisms or enzymes seems to be suggested from experience in the preparation of 6-amino-penicillanic acid (6-APA) from penicillin. However, no reports on the production of 7-ACA or D-7-ACA from cephalosporin C. on an industrial scale have been hitherto made. It is theorized that this is due to the fact that the specific group (i.e. D-5-amino-5-carboxy-pentanoyl group) is present in the side chain in the 7-position of cephalosporin C., and thus it would be expected that it would be difficult or impracticable to carry out the direct deacylation enzymatically.

In U.S. Pat. No. 3,239,394 a process is proposed for the preparation of 7-ACA from cephalosporin C. by the use of microbial cells. This process involves treating cephalosporin C. with the cultivated cells of a certain strain of bacterium selected from the group belonging to the genera Brevibacterium, Achromobacterium, and Flavobacterium to form 7-ACA and D-7-ACA in the reaction mixture. With such a process, however, it would be difficult to expect an improvement in reaction yield due to the fact that the strains of the microorganisms used are of extremely weak deacylation activity and also the fact that the enzyme with the deacylation activity has $\beta$-lactamase activity as well, thus causing the cleavage of the $\beta$-lactam rings of both cephalosporin C. and the product 7-ACA thereof.

SUMMARY OF THE INVENTION

The inventors have made extensive studies in search of microorganisms of strong deacylation activity and have now found surprisingly that certain strains of organisms belonging to the genus Aspergillus or Alternaria possess ability to produce 7-ACA or deacetyl-7-amino-cephalosporanic acid (D-7-ACA) from cephalosporin C. itself or its derivatives. The present invention has been accomplished on the basis of this unpredictable finding. The microbiological deacylation process according to the present invention has many advantages over the prior art processes, such as, for example, the requirement of only one process step, simplified and more efficient operation, in particular, the fact that high purity of the starting materials is not necessary and the low cost of installation.

OBJECTS OF THE INVENTION

It is an object of the present invention to devise and provide a new process for the preparation of "7-amino-cephem compounds I" by subjecting homologues of cephalosporin C. known herein as "compounds II" to an enzymatic action of the cultured mycelia of mold fungi or the secondary preparation therefrom.

It is also an object of this invention to provide a process for deacylation using certain strains of organisms belonging to the genus Aspergillus or alternatively to produce 7-ACA or deacetyl-7-amino-aphalosporanic acid (D-7-ACA) from cephalosporin C. itself or its derivatives.

DESCRIPTION OF SPECIFIC EMBODIMENTS OF THE INVENTION

In the following will be described a method of quantitative determination of the 7-amino-cephem compounds I formed by treatment of cephalosporin C. or derivatives thereof with the cultured mycelia of the above described strains of microorganisms, as well as some experimental results obtained by the use of the following methods:

(A) Method of quantitative determination of the 7-amino-cephem compounds I (1) For substrates soluble in organic solvents: Reagents:
  Solution A—2% solution of phenyl acetyl chloride in acetone
  Solution B—5% aqueous sodium bicarbonate solution 1 ml of the reaction mixture from the treatment of the substrate solution with the cultivated mycelia is adjusted to pH 2.5 with 1 N hydrochloric acid and extracted (i.e. washed) twice with equal amounts of ethyl acetate. The extract is adjusted to pH 7 with an 1 N caustic soda, 0.6 ml of Solution B is added thereto at 0° C. and immediately thereafter is added 2 ml of Solution A. The mixture thus obtained is kept at 0° C. for 60 minutes. After that, the resulting reaction mixture is tested for antimicrobial activity by means of microbiological assay. For this purpose is carried out the paper disc method at 37° C. for 16 hours on an assaying plate using Bacillus subtilis ATCC 6633 as a test microorganism. Separately, with the authentic 7-amino-cephem compound, there are prepared an appropriate number of aqueous solutions of different concentrations, and each of the aqueous solutions is brought into reaction with phenylacetyl chloride in the same way as described above and the reaction product tested for antimicrobial activity in the same way as described above. Thus, the amount of the 7-amino-cephem compound in the reaction mixture sample can be read from the calibration curve made with the authentic 7-amino-cephem compound.

(2) For substrates insoluble in organic solvents:
  Reagents, etc:
    Paper chromatography:
      Filter paper—Toyo#50 filter paper of the size 2 cm × 40 cm
      Solvent system—acetonitrile : water = 4 : 1
    High voltage paper electrophoresis:
      Buffer solution—formic acid : acetic acid = 1 : 4 (The pH of the mixture is 1.9.)
      Filter Paper—Toyo #51 filter paper
      Voltage—160 V/cm
      Time—30 minutes.

An aliquot of the reaction solution of the substrate and the mycelin, or the concentrate thereof, is applied to Toyo #50 filter paper and the filter paper developed at room temperature by the descending method for 4 hours with the solvent system specified above. After that, the filter paper is air-dried and two strips of 3 cm wide are cut out from the filter paper, being cut at the portions of 7.5 cm and 13.5 cm away from the starting point of the filter paper, with said portions as centers of the strips respectively. Each of the cutouts is extracted thoroughly with 2 ml of a 0.05 M phosphate buffer solution (pH 7) and 1 ml of the extract is brought into reaction with phenylacetyl chloride and the antimicrobial activity is determined, all in the same way as described in 1). By this method the fractional quantitative determination of deacetyl-7-amino-cephalosporanic acid (D-7-ACA), developed 7.5 cm away from the starting point, and 7-ACA, developed 13.5 cm away from the starting point, can be accomplished with the result that the yields of the respective products can be calculated.

If the substrate is a cephalosporin C. Bunte salt, i.e. a compound of the general formula I wherein X stands for —S—SO$_3$M and M stands for an inorganic or organic base (see E. H. Flynn, Cephalosporins and Penicillins, page 20, 1972, Academic Press, New York and London), an aliquot of the reaction solution of the compound with the cells or its concentrate is reacted with phenylacetic acid in the same manner as described above. An aliquot of the resulting reaction solution is applied to Toyo #51 filter paper and subjected to the high voltage paper electrophoresis. After that, the filter paper is air dried and a strip of 3 cm wide is cut out from the filter paper, being cut at the portion of 6 cm away from the starting point on the anode side of the filter paper, with said portion as center of the strip.

The cutout is extracted and the antimicrobial activity of the extract is determined all in the same way as described above. In this way, the 7-ACA Bunte salt formed can be quantitatively determined through the antimicrobial activity of the phenylacetylated derivative thereof.

(B) Some experimental results

As will be clearly shown in Table 1, 7-ACA and deacetyl-7-amino-cephalosporanic acid (D-7-ACA) were found to be produced by the deacylation of cephalosporin C. with the mycelial enzyme. Further, the latter, i.e. D-7-ACA, was found to be the predominent products. This is attributable to the fact that in the cultivated mycelia having deacylation activity is contained, in addition to the deacylating enzyme, an enzyme capable of hydrolyzing the ester bond of the 3-acetoxy group in cephalosporin C., i.e. an acetyl esterase. The strength of the enzymatic activity of this acetyl esterase varies with the strain of the microorganisms used. Thus, for example, Aspergillus sp. MA-13 shows a strong enzymatic activity of this enzyme with the result that D-7-ACA is preferentially produced, while Alternaria sp. MA-133 shows a relatively weak activity of the enzyme with the result that 7-ACA is produced more preferentially than D-7-ACA.

In addition, as will be shown in Table 2, the cultivated mycelia of the above described strains of microorganisms were found to exert the deacylation action not only on different N-derivatives of cephalosporin C. to produce the corresponding 7-amino-cephem compounds, but also on cephalosporin C. Bunte salts (i.e. derivatives of cephalosporin C. bearing thiosulfuric acid residues at the 3-position) to form the corresponding 7-ACA Bunte salts. (i) A mass of 0.5 g (wet weight) of the culture obtained by cultivating each of the stated mold strains in the same manner as will be described in Example 1 using Medium 1 or Medium 2 as will be specified also in Example 1 and an aliquot of 10 ml of a 0.5% aqueous solution (pH 7) of cephalosporin C. sodium salt are placed in a test tube and so much sodium azide is added thereto as to give a concentration of 100 Hg/ml. The contents in the test tube are brought into reaction by shaking the test tube at 28° C. for a period of 16 hours on a tube shaker. After that, the reaction mixture is filtered and the filtrate is subjected to the quantitative determination of 7-ACA and D-7-ACA in accordance with the above-mentioned method 2). The yields of the respective products are expressed in terms of percentages with respect to the amount of the substrate used. The results are set forth in the following Table 1

Table 1

| Strains | Medium | Yields of 7-amino-cephem compds. | | |
|---|---|---|---|---|
| | | 7-ACA | D-7-ACA | Total |
| Aspergillus sp. MA-13 (FERM - P 3490) or (ATCC No. 20491) | 2 | 0 | 18.5 | 18.5 |
| Aspergillus sp. MA-76 (FERM - P 3491) | 1 | 5 | 11 | 16 |
| Alternaria sp. MA-133 (FERM - P 3492) or (ATCC No. 20492) | 1 | 4.5 | 3 | 7.5 |
| Aspergillus niger MA-308 (FERM - P 3493) | 2 | 0 | 6.5 | 6.5 |

(ii) Aspergillus sp. MA-13 (FERM-P 3490) (ATCC No. 20491) is cultivated in the same manner as will be described in Example 1 using Medium 2 as will be specified also in Example 1. The resulting culture of the mold strain is brought into reaction with different substrates at 30° C. for 16 hours in the same way as in the case of (i). The reaction mixture is filtered and the filtrate is subjected to the quantitative determination of the 7-amino-cephem compound formed in accordance with the above mentioned methods (1) and (2). The yields of the product D-7-ACA are expressed in terms of percentages with respect to the amount of the substrate used. The results are set forth in the following Table 2.

Table 2

| Substrate | Yield of D-7-ACA |
|---|---|
| N-formyl-cephalosporin C. | 12 |
| N-(2-chloroethoxycarbonyl)-cephalosporin C | 11.5 |
| N-(p-chlorobenzoyl)-cephalosporin C. tetraethylenediamine salt | 8 |
| N-phenylcarbamoyl-cephalosporin C. | 8 |
| N-phthaloyl-cephalosporin C. | 11 |
| Deacetyl-cephalosporin C. sodium salt | 18.5 |
| Cephalosporin C. Bunte salt | 5* |

*The product is the-corresponding Bunte salt.

The inventors have tested different type cultures of mold fungi for deacylation activity to find that although in general weaker than in the selected strains indicated above the deacylation activity is found, in principle, widely in varied mold fungi. Examples of such molds include the genera Penicillium, Chaetomium, Gibberella, Macrosporium, Rhizoctonia, Glomerella, Sclerotinia and Microascus.

It is to be noted that the greatest advantage of the novel process of deacylation by the use of the cultures of mold fungi of the types described above or the secondary preparations therefrom is in the fact that little $\beta$-lactamase is found in the reaction system which otherwise would cleave the lactam ring in the compound II used as the substrate or in the 7-amino-cephem compound I produced therefrom, thus leading to efficient formation and accumulation of the product 7-amino-cephem compound I. In this respect, the process in accordance with the present invention is advantageous over the prior art such as bacterial processes accompanied by the drawback of $\beta$-lactamase activity.

Although there may be many strains of mold fungi having the ability as described above, there are shown in the following a few of them which were first isolated by us from the samples or soil or plant collected from Okayama and Hiroshima Prefectures, Japan, as well as their microbiological properties.

Aspergillus sp. MA-13

1. Growth on agar:
When grown on a potato-glucose-agar plate at 26° C. for 7 days, the strain forms a colony, 56 mm in diameter, with the white mycelium spreading radially. The colony assumes a velvety appearance and a sparse population of black spores are formed around the center of the mycelium.

When cultured on a Czapeck's agar plate in the same way as described above, the strain forms a colony, 42 mm in diameter, assuming a velvety appearance. Spores, brown in color, occur around the centers of the mycellium.

The microscopic observation shows the following morphological properties: Numerous conidia, brown in color, densely occur with the mature conidial heads, 30 to 50 $\mu$ in diameter. The conidiophores are 200 to 300 $\mu$ in length and almost upright, bearing spherical vesicles, 3 to 4 $\mu$ in diameter, at their tips. The sterigmas consists of two portions and the conidia are spherules, 3 to 4 $\mu$ in diameter, having no projections.

2. Physiological properties:
Optimal temperatures for growth: The strain grows at temperatures in the range of from 15 to 42°C. with the optimal temperature around 35°C..

Optimal pH for growth: The strain can grow at pH values in the range of from 2 to 8 with the optimal pH in the range of from 3 to 6.

Nitrate anabolism test: Negative.

From the above-described microbiological properties, the strain was identified as belonging to the genus Aspergillus sp.

Aspergillus sp. MA-76

1. Growth on agar

When grown on a potato-glucose-agar plate at 26°C. for 7 days, the strain forms a colony, 80 mm in diameter. The hyphae are extremely short and white in color and bear numerous green spores, assuming a velvety appearance.

When cultured on Czapeck's agar plate in the same way as described above, the strain forms a colony, 61 mm in diameter, and the growth assumes an appearance like a yellowish brown velvet.

The morphological observation shows the following morphological properties. In the immature stage, the conidial heads assume a broom-like appearance as their vesicles are oval in shape. When matured, the growth had conidial heads, 30 to 50 $\mu$ in diameter, and vesicles which are almost in the form of spherules, 15 to 20 $\mu$ in diameter. The conidiophores are 250 to 300 $\mu$ in length, bearing small verruciform projections around the periphery. The sterigmas consist of one portion and the conidia are 3–4 $\mu$ in diameter, bearing no small projections.

2. Physiological properties

Optimal temperature for growth: The strain can grow at temperature in the range of from 15° to 42° C. with the optimal temperature around 35° C.

Optimal pH for growth: The strain can grow at pH values in the range of from 2.5 to 9 with the optimal pH in the range of from 3 to 6.

From the above described microbiological properties, the strain was identified as belonging to the genus Aspergillus sp.

Alternaria sp. MA 133

1. Growth on agar

When cultured on a potato-glucose-agar plate at 26° C for 7 days, the strain forms a colony, 40 mm in diameter, with the periphery greenish dark black in color. The colony assumes a fluffy cottony appearance and shows little spore formation.

When cultivated on a Czapeck's agar plate in the same way as described above, the strain forms a colony, 22 mm in diameter, with the periphery, grayish black in color, curling clockwise. Around the center of the colony is found a dense population of mycelium, pale brown in color, showing spore formation.

When cultured on a medium consisting of agar-fixed falled leaves of broad-leaved trees, the growth shows very active spore formation. The microscopic observation shows that multicellular conidia of brick construction occur singly or in chains.

The spores are 8–10 × 15–20 $\mu$ in size and oval or football shaped. When matured they bear marked small projections on their surfaces and look as if cut crosswise with one to three septa. Some spores are found to have vertical septa. Besides these spores, formation of oval chlamydospores, reddish brown in color, is also found.

2. Physiological properties

Optimal temperature for growth: The strain can grow at temperature in the range of from 5 to 30° C. with the optimal temperature around 25° C.

Optimal pH for growth: The strain can grow at pH values in the range of from 3.5 to 10 with the optimal pH around 6.

From the above-described microbiological properties, the strain was identified as belonging to the genus Alternaria sp.

Aspergillus niger MA-308

1. Growth on agar

When cultured on a potato-glucose-agar plate at 26° C. for 7 days, the strain forms a colony, 63 mm in diameter. The mycelium are white in color and assume a fluffy cottony appearance, forming numerous spores, black in color.

When grown on a Czapeck's agar plate in the same way as described above, the strain forms a colony, 54 mm in diameter. The mycelium show a white color slightly mixed with a yellowish green color, assuming a fluffy cotton appearance. They are somewhat longer than those mycelium which develop on the potato-glucose-agar plate, and form numerous spores, dark brown in color.

The microscopic observation shows the following morphological properties: A dense population of conidia, black in color, occur and their mature conidial heads are spherules, 50 to 70 $\mu$ in diameter. The conidiophores are 150 to 250 $\mu$ in length and almost upright with spherical vesicles having diameters of from 20 to 40 $\mu$ at their tips. The sterigmas consists of two portions and the conidia take the form of spherules, 3 to 4 $\mu$ in diameter, bearing marked small projections.

2. Physiological properties.

Optimal temperature for growth: The strain can grow at temperatures in the range of from 15° to 42° C. with the optimal temperature around 35° C.

Optimal pH for growth: The strain can grow at pH values in the range of from 2 to 10 with the optimal pH in the range of from 3 to 6.

From the above-described microbiological properties, the strain was identified as belonging to the genus Aspergillus, and further, on the basis of Raper & Fennel, "The Genus Aspergillus", Williams & Wilkins Co., Baltimore, as belonging to the species Aspergillus niger.

The four mold strains the microbiological properties of which are set forth in the foregoing, i.e. Aspergillus sp. MA-13, Aspergillus sp. MA-76, Alternaria sp. MA-133 and Aspergillus niger MA-308, are the first useful ones which are found to produce cephalosporin C. acylase. They have been deposited with Fermentation Research Institute, Agency of Industrial Science and Technology, Japan, and have the assigned numbers FERM-P 3,490; 3,491; 3,492; and 3,493, respectively. The strains, Aspergillus sp. MA-13 and Alternaria sp. MA-133 have also been deposited with the American Type Culture Collection, U.S.A., and been assigned the ATCC numbers 20941 and 20942, respectively.

As in the case of other strains of microorganisms in general, the mold strains described above are subject to change in their properties. For example, mutants or variants can be produced from such strains by artificial means, such as, for example, ultraviolet rays, high-frequency waves, radioactive rays, or chemical mutagens. These mutants or variants can be used in the process in accordance with the present invention so far as they are of capacity for the desired deacylation.

In preparing the desired 7-amino-cephem compounds I by the use of the mold strains mentioned above, it is preferred to cause the cultures obtained by culturing these microorganisms, or the secondary preparations therefrom, to act on the compounds II under appropriate conditions.

For the purpose of obtaining the cultures, there may be employed conventional cultivation methods wherein culture media containing nutrients usually utilizable by microorganisms are used. As nutrient sources, there may be employed any sources which are in use in cultivation of microorganisms in general. For example, as carbon sources, there may be used, for example; glucose, sucrose, starch, glycerin, corn syrup, molasses and soybean oil. Examples of suitable sources of nitrogen include soybean meal, wheat embryo, meat extracts, peptone, corn steep liquor, dry yeast, ammonium sulfate and sodium nitrate. In addition to these sources, there may be used, in any appropriate combination, those additives which serve to aid the growth of the microorganisms and which are necessary for enhancement of the deacylation ability, that is, for acceleration of production of cephalosporin C. acylase activity. Examples of such additives include sodium chloride, potassium chloride, calcium carbonate, phosphates and the like inorganic salts. As cultivation method, there may be employed any conventional procedure employed for microorganisms in general wherein a solid or liquid medium is used. For production on an industrial scale is particularly suitable the submerged culture.

The cultivation is carried out under aerobic conditions at a temperature in the range of from 25° to 37°C., preferably approximately 28° C. The time of cultivation depends on other cultivation conditions, especially the cultivation equipment and the composition and temperature of the medium, and is preferably chosen in such a manner that the cultivation is stopped at the point of time when the deacylation activity of the culture reaches the maximum. In the case of Aspergillus sp. MA-13, for example, the acylace activity begins to appear at the third day and reaches the maximum at the fourth to fifth day of cultivation, decreasing thereafter until it disappears, although somewhat depending on the kind and concentration of the medium. In general the time of cultivation is preferably in the range of from 3 to 7 days.

As mentioned above, the culture of the secondary preparation therefrom is used for the deacylation of the compounds II. The "secondary preparation from the culture" or equivalent expressions thereof as used herein mean any product which is obtained by subjecting the culture to such a treatment as to give a type of product which increases the efficiency of production of the desired 7-amino-cephem compounds I, in other words, is advantageous for the production of the desired compounds. Thus, since what is of essential importance for the deacylation in accordance with the process of the invention is the enzyme which can be called "cephalosporin C. acylase", there may be used a diversity of secondary preparations having an activity of cephalosporin C. acylase. Examples of such secondary preparations include the following: mycelia obtained by collection from the culture broth followed by washing; cell-free extracts obtained by application of physical or chemical treatments to mycelia (for example, disruption products obtained by grinding or ultrasonic treatment of mycelia, and mycelial lysates obtained by treatment with surface active agents or enzymes); partially or perfectly purified preparations of the desired enzyme obtained by purifying the cell-free extracts by known methods of enzyme purification, such as, for example, salting out, fractional precipitation, dialysis, gel filtration, and ion exchange or adsorption chromatography; products with the deacylating activity obtained by linking the enzyme, either physically or chemically, to water-insoluble high molecular substances; and products with the 7-amino-cephem compounds I-producing activity obtained by adsorbing washed mycelia on Celite or water-insoluble high molecular substances.

The preparation of the compounds I from the compounds II by the deacylation by the use of the cultures or their secondary preparations is carried out in general in an aqueous medium. Before referring in more detail to the reaction conditions, some of the properties of the intracellular enzyme found in the culture, i.e. "cephalosporin C. acylase" are set forth in the following. The enzyme exhibits the deacylating activity at pH values in the range of from 6 to 8, with decreased or no activity shown at pH values lower than 5 or higher than 9. The enzyme functions at temperatures in the range of from 28° to 40°C., losing its activity at temperatures higher than 50° C. Therefore the enzymic reaction is preferably carried out at pH values in the range of from 6.5 to 7.5 and temperatures in the range of from 28° to 40° C. Further, the activity of the enzyme can be inactivated by enzyme inhibitors such as EDTA (ethylenediaminetetraacetic acid).

When the culture or the secondary preparation therefrom is insoluble in water, the reaction is carried out in a system taking the form of a suspension, whereupon it is effective to apply appropriate shaking or stirring. Alternatively, the culture or the secondary preparation therefrom may be filled in a column so that the desired deacylation reaction can be caused to occur continuously during passage of an aqueous solution of the compound II through the column. The reaction time will depend on different factors, such as, for example, the substrate concentration, the activity of the deacylating enzyme and the reaction temperature, although it is in general in the range of from 6 to 60 hours. It is advisable to predetermine, by a pretest, the time required for the maximal production of the 7-amino-cephem compound I and to determine the reaction time on the basis of the pretest result. The substrate concentration will depend predominantly on the potency of the deacylating activity, although it is appropriately in the range of from 0.1 to 10%. In addition, it is also possible, in order to prevent the reaction system from contamination with foreign microorganisms during the reaction, to use an appropriate anticontamination agent.

The 7-amino-cephem compounds I prepared by causing the cultures of strains of the microorganisms mentioned above, or secondary preparations therefrom, to act on the compounds II in the presence of an aqueous medium can be purified by any known method. Thus, the end product may be purified, for example, by ion exchange chromatography, column chromatography or isoelectric precipitation. It may also be purified by the method wherein the finally resulting reaction mixture is, optionally in the course of a further purification stage, brought into reaction with an appropriate organic acid or the like to form a derivative of the end product, wherein the end product is converted into a water-insoluble salt which is then extracted with an organic solvent, or wherein the end product is converted into a form suitable for subsequent isolation from the reaction mixture. These methods of purification, of course, may be employed in any appropriate combination.

In the following examples, unless otherwise indicated, parts and percentages are by weight, and the relationship of parts by weight to parts by volume is that of grams to cubic centimeters.

EXAMPLE 1

Medium 1: 2% glucose, 1% peptone, pH 7 (before sterilization)

Medium 2: 2% glucose, 1% corn steep liquor, 1% peptone, 0.1% potassium secondary phosphate, 0.5% calcium carbonate pH 6.5 (before sterilization).

Each of four 500 ml Sakaguchi's flasks was charged with 100 ml of Medium 1 and sterilized in an autoclave at 120° C. for 15 minutes. One loop of Aspergillus sp. MA-76 (FERM-P 3491) inoculum was applied to each of the media and subjected to shake culture at 28° C. for 4 days on a reciprocal shaker. The cultures were filtered and washed with water to obtain a washed mycelial mass. 10.5 g wet weight of the mycelial mass and 400 ml of a 0.5% aqueous solution (pH 7) of cephalosporin C. sodium salt of 85% purity were placed in a 1 liter Erlenmeyer flask. 40 mg of sodium azide was added to the mixture and the reaction was carried out with stirring for 22 hours in a water tank kept at a constant temperature of 30° C. The reaction mixture was filtered and the mycellal mass was washed finally to obtain 420 ml of the reaction mixture consisting of the filtrate and the washings. The reaction mixture was adsorbed on a column of 120 ml of DEAE=Sephadex A-25 (chloride form; manufactured by Pharmacia) and the column was washed with 120 ml of distilled water and eluted with a linear gradient increase in sodium chloride concentration of up to 0.1 M. The mixing chamber contained 500 ml of distilled water and the reservoir contained 500 ml of 0.1 M NaCl solution). The effluent was collected as fractions each containing a 19 ml portion. Fractions Nos. 52 through 60 (7-ACA fractions) and fractions Nos. 63 through 75 (D-7-ACA fractions) were separately combined and concentrated to volumes of 2 ml and 6 ml, respectively. The respective fractions were adjusted to pH 4.2 with hydrochloric acid and allowed to stand overnight at 5° C. The precipitates formed were separated by centrifugation, washed with small quantities of distilled water and dried to give 35 mg of 7-ACA of 90% purity and 117 mg of D-7-ACA of 95% purity. The yields, based on the substrate used, of 7-ACA and D-7-ACA were 3% and 12.4%, respectively, the total yield being 15.4%.

Similar results are obtained if Medium 2 is used in the process of Example 1.

EXAMPLE 2

8.7 g (wet weight) of the mycelial mass obtained by cultivating Aspergillus sp. MA-13 (FERM-P 3490) (ATCC No. 20491) is Medium 2 in the same manner as described in Example 1 was filled in a column, 4.2 cm in diameter and 28 cm in height. The top and bottom openings of the column were connected with each other to form a closed reaction system. 200 ml of a 0.5% aqueous solution (pH 7) of cephalosporin C. sodium salt of 85% was passed through the column downward from the top and circulated through the closed reaction system at a flow rate of 2 ml/minute by using a Perpex pump (LKB, Produktor A.B., Sweden) in such a way as to ensure good contact of the substrate solution with the mycelial mass. The reacting system was held for 17 hours in a water tank kept a constant temperature of 30° C. After that, the mycelial mass was separated from the reaction mixture and washed with water. The reactions solution and the washings were combined to give a total volume of 220 ml. The resulting solution was passed through a column of 60 ml of DEAE-Sephadex A-25 (chloride form). The column was first washed with water and then eluted with linear gradient increase in sodium chloride concentration from 0 up to 0.1 M in the same manner as in Example 1 to collect D-7-ACA fractions. The combined D-7-ACA fractions were concentrated and purified by the isoelectric precipitation method as in Example 1 to give 90 mg of D-7-ACA of 90% purity. The yield, based on the substrate used, of D-7-ACA was 18.1%.

EXAMPLE 3

A mass of 10 g (wet weight) of the mycelial mass obtained by cultivating Aspergillus sp. MA-76 (FERM-P 3491) in Medium 2 in the same manner as described in Example 1 and 195 ml of a 0.6% aqueous solution (pH 7.2) of N-(2,4-dinitrophenyl)-cephalosporin C. were placed in a 500 ml Erlenmeyer flask. 21 mg of sodium azide was added to the mixture. The reaction was carried out with stirring for 16 hours in a water tank kept at a constant temperature of 37° C. The mycelial mass was filtered off from the reaction mixture and washed with water. The filtrate and the washings were combined to give a total volume of 210 ml. The resulting solution was adjusted to pH 2.5 by the addition of 5N hydrochloric acid and extracted twice with equal volumes of ethyl acetate. The aqueous phase was adjusted to pH 7 by the addition of 5 N caustic soda and passed through a column of 60 ml of DEAE-Sephadex A-25 (chloride form). The column was washed with 60 ml of distilled water and eluted with a linear gradient increase in sodium chloride concentration from 0 up to 0.2 M in the same manner as described in Example 1. The effluent was collected as fractions each containing a 5 ml portion. Fractions Nos. 37 through 41 (7-ACA fractions) and fractions Nos. 43 through 50 (D-7-ACA fractions) were separately combined concentrated and purified by the isoelectric precipitation method as in Example to give 18 mg of 7-ACA of 90% purity and 75 mg of D-7-ACA of 90% purity, respectively. The overall yield, based on the substrate used of the resulting 7-amino-cephem compounds was 17.6%.

While specific embodiments of the invention have been shown and described in detail to illustrate the application of the principles of the invention, it will be understood that the invention may be embodied otherwise without departing from such principles.

What is claimed is:

1. Process for the preparation of 7-amino-cephem compounds of the general formula I

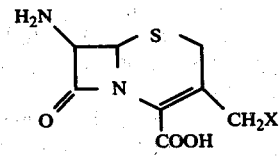

wherein X stands for a hydroxyl group, an acetoxy group or a thiosulfuric acid residue, from compounds of the general formula II

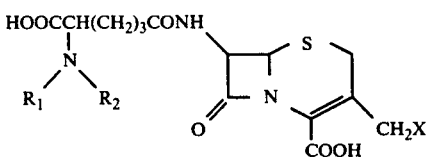

wherein $R_1$ stands for hydrogen, a lower alkanoyl group, an arylalkanoyl group, an alkoxycarbonyl group, a lower haloalkoxycarbonyl group, a substituted or unsubstituted aroyl group, a N-arylcarbamoyl group or a substituted or unsubstituted aryl group, $R_2$ either means hydrogen or forms, together with the

group, a phthalimido group, and X stands for a hydroxyl group, an acetoxy group or a thiosulfuric acid residue, or their metals salts or their salts with organic bases, which process comprises causing the culture of a microorganism selected from the group consisting of Aspergillus sp. MA-13 and Alterneria sp. MA-133 to act on a substrate compound of the general formula II in the presence of an aqueous medium.

2. Process according to claim 1, wherein the microorganism consists essentially of Aspergillus sp. MA-13 (FERM-P3490) ATCC No. 20491.

3. Process according to claim 1, wherein the microorganisms consists essentially of Alternaria sp. MA-133 (FERM-P3492) ATCC No. 20492.

4. Process according to claim 1, wherein the microorganism acts on the substrate compound at pH values in the range of 6.5 to 7.5.

5. Process according to claim 1, wherein the microorganism acts on the substrate compound at temperatures in the range of 28° C. to 40° C.

6. Process according to claim 1, wherein the microorganism acts on the substrate compound during a time from about 6 to about 60 hours.

7. Process according to claim 1, wherein the substrate compound's concentration is in the range of from 0.1 to 10% by weight.

8. Process according to claim 1, wherein an anticontamination agent is added to the medium to prevent the reaction system from being contaminated with foreign microorganisms.

* * * * *